(12) United States Patent
Singh et al.

(10) Patent No.: US 8,173,390 B2
(45) Date of Patent: May 8, 2012

(54) METHOD FOR FACILITATING FERMENTATION OF HIGH SOLIDS COMPOSITIONS

(75) Inventors: Vijay Singh, Savoy, IL (US); Jameel K. Shihadeh, Downers Grove, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 406 days.

(21) Appl. No.: 12/576,309

(22) Filed: Oct. 9, 2009

(65) Prior Publication Data

US 2010/0143966 A1 Jun. 10, 2010

Related U.S. Application Data

(60) Provisional application No. 61/104,316, filed on Oct. 10, 2008.

(51) Int. Cl.
*C12P 1/00* (2006.01)
(52) U.S. Cl. ........................................................ 435/41
(58) Field of Classification Search ..................... 435/41
See application file for complete search history.

(56) References Cited

OTHER PUBLICATIONS

Cysewski, G.R. and Wilke, C.R. "Rapid Ethanol Fermentations Using Vacuum and Cell Recycle" Biotechnology and Bioengineering 1977 vol. 19: 1125-1143.
Ramalingham, A. And Finn, R.K. "The Vacuferm Process: A New Approach to Fermentation Alcohol" Biotechnology and Bioengineering 1977 vol. 19: 583-589.
Wang et al. "Optimization of Fermentation Temperature and Mash Specific Gravity for Fuel Alcohol Production" Cereal Chemistry 1999 vol. 76(1): 82-86.
Wang et al. "Comparison of Raw Starch Hydrolyzing Enzyme with Conventional Liquefaction and Saccharification Enzymes in Dry-Grind Corn Processing" Cereal Chemistry 2007 vol. 84(1): 10-14.
Maiorella et al. "Rapid Ethanol Production Via Fermentation" University of California Lawrence Berkeley Lab Nov. 1979 LBL 10219: 1-28.
Stargen Product Information Brochure Jun. 2005 (Genencor, Palo Alto, CA).

*Primary Examiner* — Herbert J Lilling
(74) *Attorney, Agent, or Firm* — Licata & Tyrrell P.C.

(57) ABSTRACT

The present invention features a method for facilitating the fermentation of a high solids composition. The method involves subjecting the high solids composition to granular starch hydrolyzing enzyme during the fermentation process to provide a steady source of glucose. Moreover, the instant method is carried out under reduced pressure to selectively remove volatile components such as ethanol and water from the fermentation vessel.

5 Claims, 2 Drawing Sheets

METHOD FOR FACILITATING FERMENTATION OF HIGH SOLIDS COMPOSITIONS

INTRODUCTION

This application claims the benefit of priority from U.S. Provisional Application Ser. No. 61/104,316 filed Oct. 10, 2008, which is herein incorporated by reference in its entirety.

BACKGROUND OF THE INVENTION

By the end of 2007, the U.S. produced 6.5 billion gallons of ethanol per year from 139 dry grind corn plants, a 32% increase in production from the previous year (RFA (2008) Ethanol industry outlook. Renewable Fuels Association: Washington, D.C.). In the dry grind process, corn is ground and slurried to approximately 32% solids (wb). The slurry is incubated at 105° C. for several minutes to gelatinize starch and at 90° C. with amylases to break down hydrated starch to dextrins. Yeast, urea and glucoamylases are added to this mash which undergoes simultaneous saccharification and fermentation (SSF) whereby yeast anaerobically convert sugars to ethanol. Ethanol is removed during distillation and remaining solids are dewatered and dried to produce distillers dried grains and solubles (DDGS).

Figure 1A:
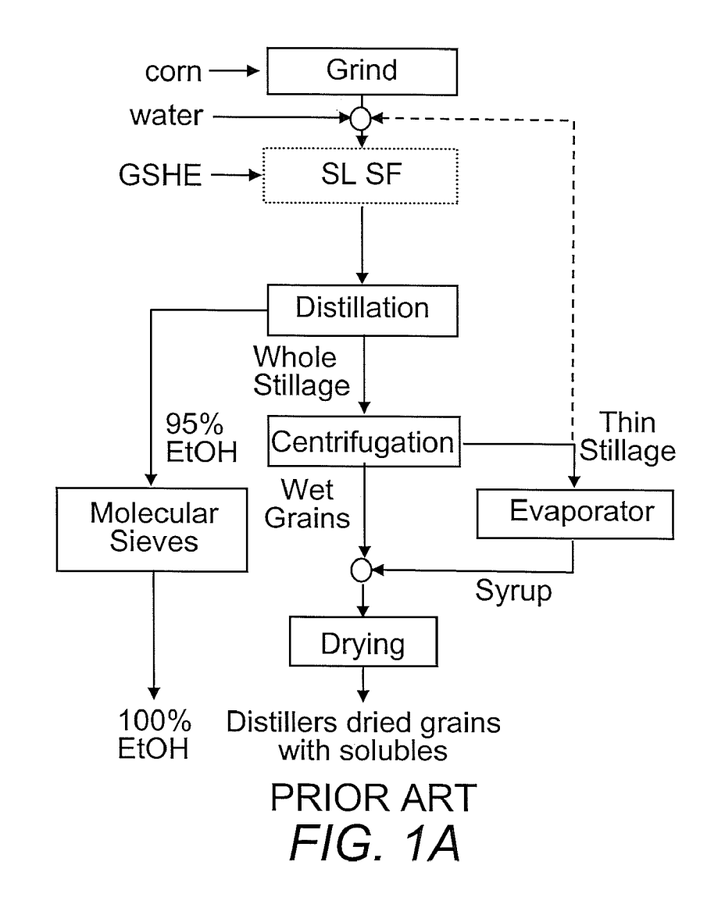
FIG. 1A depicts a strategy for high solid fermentation using a granular starch hydrolyzing enzyme process. In this process, cooking and liquefaction operations of conventional dry grind ethanol production are combined with simultaneous saccharification and fermentation to produce simultaneous liquefaction saccharification and fermentation.

Though yeast productivity is dependent on a number of environmental and process factors, dry grind operations are designed with substrate and end-product inhibition of yeast in mind. The inherent release of glucose during cooking requires initial slurry solids $\leq$32% (w/w). This limit results from two factors: controlling mash viscosity after cooking and keeping glucose concentrations below inhibitory levels (typically 15 to 16% (w/v) (Thatipamala, et al. (1992) *Biotechnol. Bioeng.* 40:289-297). A granular starch hydrolyzing enzyme (GSHE) digests raw starch to glucose at $\leq$48° C. By gradually liquefying starch during fermentation, GSHE renders starch cooking unnecessary and avoids viscous- and inhibitory-based solids content limits imposed by glucose. The consolidated process is called simultaneous liquefaction saccharification and fermentation (SLSF) (FIG. 1A). It has been reported that using GSHE resulted in comparable yields to conventional enzymes and methods at 25% solids (Wang et al (2007) *Cereal Chem.* 84:10-14). GSHE permits higher solids fermentations; however, it has not be determined whether GSHE SSF fermentations can be performed at solids >32% (w/v).

Higher solids fermentations result in higher ethanol concentrations. Early onset of ethanol inhibition caused by using higher solids reduced yield and fermentation efficiency (Wang, et al (1999) *Cereal Chem.* 76:82-86). Therefore, in situ removal of ethanol, using technologies such as vacuum stripping, could slow ethanol accumulation and reduce early inhibition (Ramalingham and Finn 1977, Cysewski and Wilke 1977). By applying vacuum at 6.7 kPa (28 inHg) and increasing fermentation yeast densities, 12-fold higher productivities and successful fermentations at 35% glucose (w/w) have been reported (Cysewski & Wilke (1977) *Biotechnol. Bioeng.* 19:1125-1143), wherein normal glucose feeds are closer to 10% (w/w). Vacuum application, however, was found to cause strict anaerobiosis ($O_2$<8 ppm), inducing nutritional deficiencies with yeast. Sparging with oxygen was expensive while sparging with air, though cheap, required a large vacuum pump to recompress $N_2$. Therefore, the Flash-ferm has been proposed (Maiorella, et al (1979) *Rapid ethanol production via fermentation*. Rep. No. 10219. Univ. Calif. Lawrence Berkeley Lab: Berkeley, Calif.), wherein beer is pumped continuously between the fermenter at atmospheric pressure and a flash vessel. Vacuum (6.7 kPa) is applied to the flash vessel instead of the main fermenter vessel. With this strategy the fermenter can be sparged with air without requiring a large vacuum compressor.

Processes developed by Ramalingham & Finn ((1977) *Biotechnol. Bioeng.* 19:583-589), Cysewski & Wilke ((1977) supra), and Maiorella, et al. ((1979) supra) use a glucose feedstock and continuous fermentation whereas most modern dry grind plants use ground corn and batch fermentations. If higher solids are anticipated, circulating beer to a flash vessel may pose difficulties with pumping the beer. Furthermore, modern technologies have overcome sparging requirements. While older yeast strains require air sparging for lipid production (Andreasen & Stier (1953) *J. Cell. Physiol.* 41:23-36), newer strains contain sufficient lipids for batch fermentation (D'amore & Stewart (1987) *Enzyme Microb. Technol.* 9:322-330; You, et al. (2003) *Appl. Environ. Microbiol.* 69:1499-1503).

SUMMARY OF THE INVENTION

The present invention features a method for facilitating the fermentation of high solids by subjecting a fermenting high solids composition to granular starch hydrolyzing enzyme under reduced pressure. In one embodiment, the high solids composition is at least 40% solids. In another embodiment, the method is carried out in the absence of liquefaction and jet cooking steps. In a further embodiment, the granular starch hydrolyzing enzyme (GSHE) is employed at a rate of at least 0.75% weight GSHE per weight dry plant material. In particular embodiments, the reduced pressure is applied at intervals during fermentation.

BRIEF DESCRIPTION OF THE DRAWINGS

FIG. 2 is a schematic of a vacuum stripping and fermentation apparatus. TC is thermocouple, HX is tube heat exchanger, DC is motor, → is check valve, SSR is solid state relay, P are pressure gages.

DETAILED DESCRIPTION OF THE INVENTION

Figure 1B:
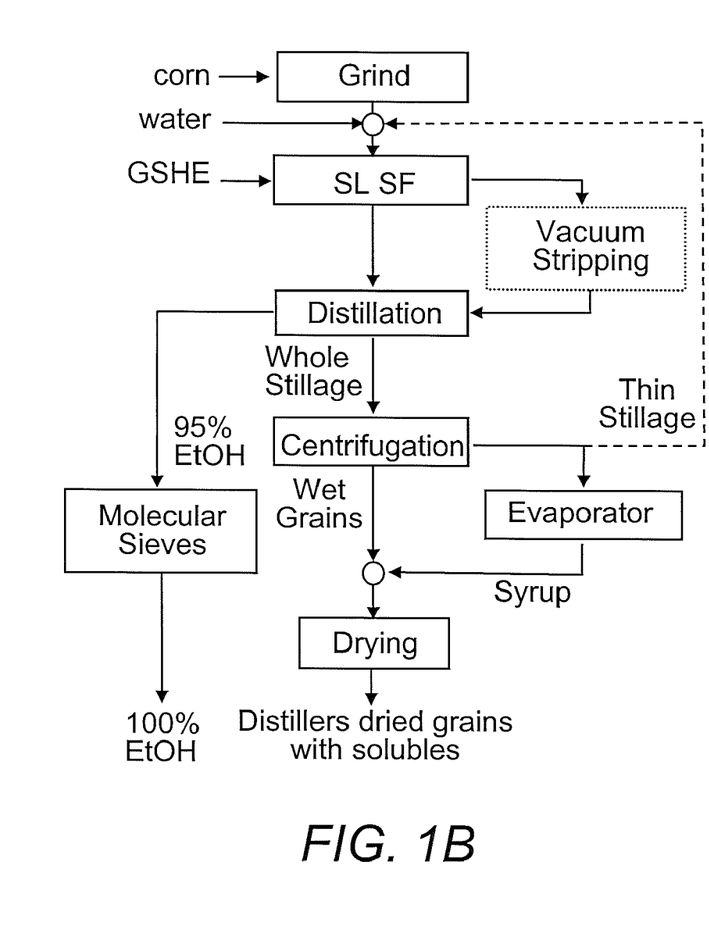
FIG. 1B depicts a strategy for high solid fermentation using a vacuum stripping process. In this process, reduced pressure is applied continually to a GSHE fermentation to remove ethanol and water.

It has now been found that combining vacuum cycling with higher solids fermentations (FIG. 1B) poses several advantages over conventional dry grind methods. For example, lower ethanol concentrations can improve yeast productivity and ethanol yield. Furthermore, this process can offer opportunities to reduce capital and operating costs of dry grind plants. For example, the jet cooking step is unnecessary with GSHE. Also, higher solids reduce the load on dewatering equipment and related capital (Taylor, et al. (2000) *Biotechnol. Progr.* 16:541-547) and can permit direct selling of stillage as wet grains without dewatering.

Accordingly, the present invention features a method for facilitating high solids fermentation by simultaneously subjecting a high solids composition to saccharification and fermentation in the presence of GSHE and reduced pressure conditions (i.e., vacuum stripping). As used in the context of the present invention "high solids fermentation" refers to a fermentation reaction, wherein the composition contains at least 32%, 33%, 34%, 35%, 40%, 45%, 50%, or more solid matter (e.g., solid plant material) on a weight to weight basis. Desirably, a "high solids composition" contains at least 32% or 34% solid matter. More particularly, "a high solids composition" contains 32% to 50%, or 40% to 45% solid matter. High solids compositions within the scope of the present invention include, but are not limited to, slurries of solid matter such as plant-based dry grinds. Plant-based compositions include those obtained from corn, soybean, and the like. Such substrates for fermentation are well-known to those skilled in the art and any suitable solid plant material can be employed.

As is conventional in the art, fermentation is achieved when microorganisms such as yeast (e.g., *S. cerevisiae*) or bacteria are added to a dry grind slurry (e.g., a fermenting high solids composition), whereby the microorganisms anaerobically convert sugars to ethanol. In certain embodiments, the slurry is also simultaneously subjected to saccharification, wherein hydrolases (e.g., glucoamylases) are added to the slurry to convert starch to sugars. Advantageously, when these processes are carried out in the presence of GSHE, starch in the higher solids is gradually converted to glucose, thereby providing a constant supply of glucose to the yeast at lower concentrations than is produced by liquefaction and jet cooking. Moreover, when high levels of GSHE (e.g., levels about three-fold of conventional methods) are employed ethanol yields comparable to conventional dry grind processes are produced. Thus, in particular embodiments, the GSHE is used at a rate of at least 0.75% weight GSHE per weight dry plant material. Moreover, in particular embodiments, the instant method is carried out in the absence of liquefaction and jet cooking. The reduced glucose content achieved by GSHE as compared to liquefaction and jet cooking avoids viscous- and inhibitory-based solids content limits, which are imposed by high glucose levels.

It is contemplated that the GSHE can be obtained from any suitable source and can be purchased or extracted from culture filtrates of microorganisms such as fungi (e.g., *A. kawachi* and *A. niger*) or bacteria. An exemplary GSHE is STARGEN® 001 (Genencor, Palo Alto, Calif.) composed of amylase and glucoamylase.

In accordance with the instant method, a reduced pressure environment is employed to selectively remove volatile components such as ethanol and water from the fermentation vessel. As used in the context of this invention, the term "reduced pressure" is defined as a pressure in the fermentation vessel that is less than the standard atmosphere (i.e., 101.325 kPa, 760 mmHg (torr), 29.92 inHg, 14.696 PSI, or 1013.25 millibars), wherein the minimum vacuum pressure may be dependent on fermentation temperature. In particular embodiments, "reduced pressure" is less than 90, 80, 70, 60, 50, 40, 30, 20, or 10 kPa. In particular embodiments, the pressure in the fermentation vessel is less than 10 kPa. Pressure reduction can be achieved using any conventional method, e.g., by applying a vacuum. Advantageously, carrying out fermentation of high solids material under reduced pressure was found to maximize ethanol concentration by as much as 18% to 21% volume ethanol per volume beer. In so far as higher solids produce ethanol more quickly, causing early yeast death, removal of ethanol during fermentation extends yeast viability and vitality.

Moreover, in particular embodiments, reduced pressure is applied at intervals during fermentation. Such intervals can be based on minutes, hours or days. In particular embodiments, the intervals are based on hours or days. In this regard, the step interval includes a cycle of applying a vacuum for a specified amount of time, stopping the vacuum pump, and reapplying the vacuum after several hours or days. It is contemplated that this cycle can be repeated 1, 2, 3, 4, 5, 6, 7, 8, or more times during the fermentation reaction. In particular embodiments, the vacuum is applied for 5 minutes to 60 minutes. More desirably, the vacuum is applied for 20 to 40 minutes. Most desirably, the vacuum is applied for 30 minutes. In other embodiments, the vacuum is applied every 3, 4, 5, 6, 7, 8, 9, 10, 11, or 12 hours. Indeed, the vacuum stripping frequency and length of application can vary with each solids content.

By way of illustration, the instant method was carried out with three percentages of plant material, 30, 40 and 45%. Using the instant method, foaming was observed during the start of each vacuum cycle, likely due to release of $CO_2$ in beer. Foaming was reduced with increasing solids content up to 45%.

Figure 3:
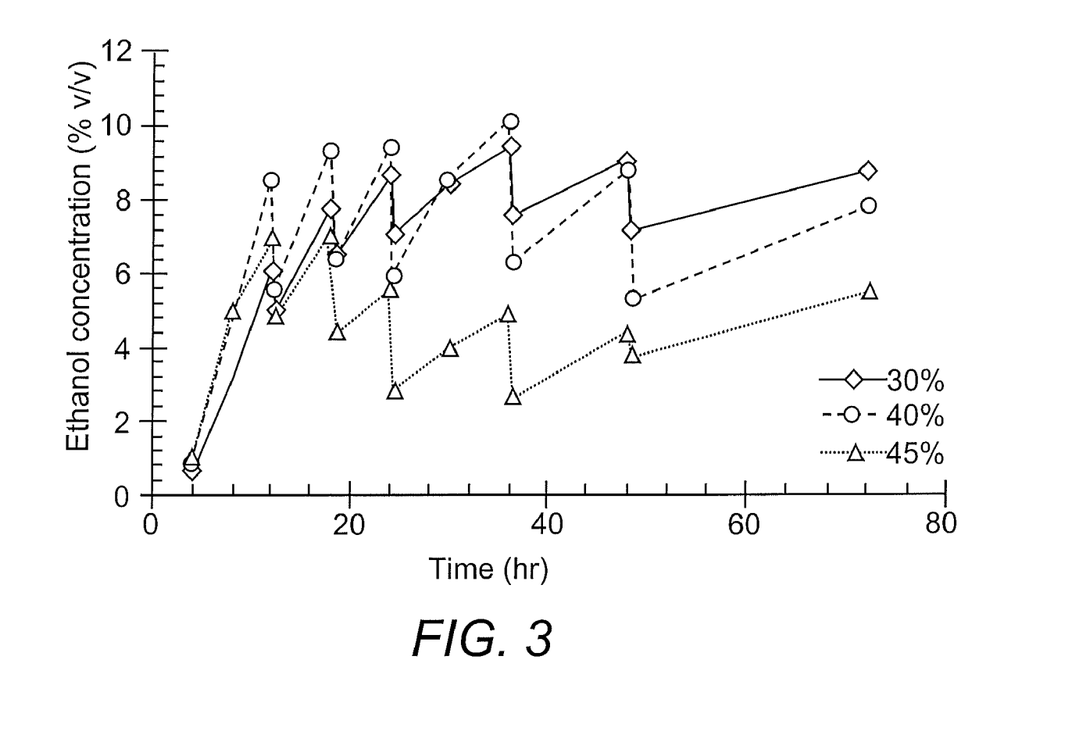
FIG. 3 shows the effect of vacuum stripping on ethanol concentrations for 30 (diamond), 40 (circle) and 45% (square) initial solids. For one treatment at each solids level, samples of beer were taken immediately after each vacuum cycle (at 12.5, 18.5, 24.5, 36.5 and 48.5 hours) to monitor the effect of vacuum cycling on beer ethanol concentration.

Ethanol concentrations fluctuated with each vacuum application (FIG. 3). Varied responses to vacuum cycling at each solids level implied the potential importance of optimizing cycle time for solids content. Further vacuum treatments did not include additional sampling after each vacuum cycle in order to reduce sources of error when comparing to conventional, non-vacuum treatments.

Fermentation profiles were analyzed. The results of this analysis indicated that ethanol concentrations of vacuum treatments remained lower throughout the fermentation compared to those of conventional treatments (FIG. 4). Final ethanol concentrations for conventional treatments ranged from 15.1 and 19.0% (v/v), while vacuum treatments ranged from 5.03 and 9.19% (v/v) although values did not correlate with solids content ($R2=0.5$). The highest values, in both cases, were from 40% solids runs. Typically, vacuum treatments had greater variability among replicates (max σ from 0.4 to 1.0% v/v) compared to conventional treatments (max σ from 0.6 to 1.0% v/v). This observation was attributed to minor fluctuations with vacuum pressure during vacuum cycling.

For conventional runs at 30% solids, final ethanol concentrations ranged from 15.1 to 15.3% (v/v) (Table 1).

TABLE 1

| Treatment | Max Ethanol % v/v | Final Ethanol[a,b] % v/v | Initial Glucose[a,c] % w/v | Final Glucose[a,d] % w/v |
|---|---|---|---|---|
| 30% Conventional |  | 15.3 ± 0.2 a | 2.85 ± 0.23 k | 0.09 ± 0.02 s |
| 30% Vacuum | 8.56 ± 0.93 | 7.65 ± 1.00 | 3.16 ± 0.20 k | 0.10 ± 0.01 s |
| 40% Conventional |  | 18.9 ± 0.1 b | 4.89 ± 0.50mn | 1.54 ± 0.11 t |

TABLE 1-continued

| Treatment | Max Ethanol % v/v | Final Ethanol[a,b] % v/v | Initial Glucose[a,c] % w/v | Final Glucose[a,d] % w/v |
|---|---|---|---|---|
| 40% Vacuum | 10.9 ± 0.5 | 9.00 ± 0.26 | 4.80 ± 0.25 m | 0.12 ± 0.01 s |
| 45% Conventional |  | 17.3 ± 0.8 c | 5.56 ± 0.27 p | 0.06 ± 0.04 s |
| 45% Vacuum | 8.29 ± 0.62 | 5.56 ± 0.46 | 5.37 ± 0.30np | 0.12 ± 0.00 s |

[a]Only conventional treatments were analyzed statistically for final ethanol concentrations as ethanol profiles for vacuum treatments did not follow a consistent trend. Fisher's LSD was 0.9% (v/v).
[b]Means followed by the same letter are similar (P < 0.05).
[c]Maximum glucose occurred typical at 4 hr. Fishers LSD was 0.54% (w/v).
[d]Fishers LSD was 0.09% (w/v).
Means of triplicate runs ± standard deviation.

For vacuum cycled treatments final ethanol concentrations ranged from 6.6 to 8.5% (v/v). Throughout fermentations using vacuum stripping, ethanol concentrations were maintained less than 10% (v/v) with maximum values between 7.5 and 9.2% (v/v), all occurring at 36 hours. Ethanol concentrations were below the inhibition range of 10 to 13% (v/v) (Casey & Ingledew (1986) supra). Final ethanol concentrations at 40% solids ranged, for conventional runs, between 18.8 and 19.0% (v/v) and, for vacuum treatments, between 8.7 and 9.2% (v/v). Maximum ethanol concentrations for vacuum cycled replicates occurred at 36 hours and ranged between 10.6 and 11.4% (v/v). For 45% solids, final ethanol concentrations of conventional runs ranged between 16.5 and 18.1% (v/v). For vacuum treatments, maximum ethanol concentrations remained below 8.8% (v/v) with final concentrations ranging between 5.0 and 5.9% (v/v).

Initial glucose concentrations, which were sampled at 4 hours, increased with higher solids contents. At this hour, yeast densities were low, so glucose consumption was lower than production by GSHE. Highest initial concentrations were similar between conventional and vacuum treatments (LSD was 0.32% w/v) but statistically different at each solids content (LSD was 0.39% w/v). The highest values observed were far below inhibition levels of 15% (w/v) (Casey & Ingledew (1986) supra; Thatipamala, et al. (1992) supra). Glucose concentrations for conventional and vacuum treatments then decreased exponentially until <0.1% (w/v) by 12 hours, typically remaining near this level through the remainder of the fermentation.

For conventional treatments at 30% solids, mean initial glucose concentration was 2.8% (w/v), similar to 3.2% (w/v) for vacuum cycled treatments (with LSD of 0.55% w/v). At 40% solids initial glucose concentrations for conventional and vacuum treatments were similar with 5.0 and 4.8% (w/v), respectively. Glucose concentrations for conventional treatments rose after 48 hours to 1.54% (w/v), which was unexpected. The rapid increase in glucose concentration suggested a reduction in yeast glucose uptake, a consequence of high ethanol concentrations increasing cell maintenance costs (Thatipamala, et al. (1992) supra). For vacuum treatments, this glucose increase was not present; final glucose concentrations were lower at 0.12% (w/v). For 45% solids, maximum glucose concentrations of 5.6 and 5.4% (w/v) for conventional and vacuum runs, respectively, were similar. Unlike 40% solids, glucose did not accumulate by completion of fermentation of 45% solids.

GSHE was dosed at 1.13 GSHU/g corn (db), constant for all solids treatments. Higher solids may reduce the efficacy of GSHE, which has been suggested to work in slurries up to 38% solids, although glucose production was observed throughout 40% solids treatments. Furthermore, as starch is hydrolyzed and consumed beer solids reduce to approximately one third of initial slurry solids (though incomplete conversions augment final beer solids). This continuous liquefaction and consumption means that, the highest solids GSHE was exposed to were at the start of the fermentation. For 45% solids treatments, glucose accumulation was observed during the first 12 hours of fermentation, implying enzymatic activity, while final beer solids were 32% (w/w), below the maximum manufacturer recommendation. The reason for the glucose increase, occurring only at 40% solids, will be evaluated. It is possible that the high initial solids encountered with 45% solids fermentations permanently reduced GSHE activity such that a glucose increase was not observed.

Fermentation rates and completion of the fermentation were also compared with conventional and vacuum stripping methods. During the first 12 hours, higher solids tended to produce higher fermentation rates (Table 2). As vacuum stripping was not applied until 12 hours, rates were similar between conventional and vacuum treatments at each solids level. Fermentation completion was compared among conventional treatments. At 24 hours, 45% solids treatment had the highest completion (75.3% of final concentration) followed by 40% solids (73.7% of final) and 30% solids (69.1% of final). At 48 hours, 40% solids treatment had highest completion (97.5% of final), followed by 45% solids (93.9% of final) and 30% solids (91.6% of final).

TABLE 2

| Treatment | Final Glycerol % v/v | Max Lactic Acid % w/v | Max Acetic Acid % w/v | Ferment. Rate[a] g/L/hr |
|---|---|---|---|---|
| 30% Conventional | 0.85 ± 0.02 | 0.09 ± 0.10 | 0.00 ± 0.00 | 5.50 ± 0.35 a |
| 30% Vacuum | 1.14 ± 0.10 | 0.07 ± 0.00 | 0.00 ± 0.00 | 5.53 ± 0.05 a |
| 40% Conventional | 1.09 ± 0.02 | 0.04 ± 0.04 | 0.00 ± 0.00 | 7.50 ± 0.64 b |
| 40% Vacuum | 1.46 ± 0.00 | 0.08 ± 0.02 | 0.03 ± 0.05 | 7.48 ± 0.16 b |
| 45% Conventional | 1.06 ± 0.05 | 0.04 ± 0.04 | 0.00 ± 0.00 | 7.27 ± 0.03 b |
| 45% Vacuum | 1.15 ± 0.11 | 0.59 ± 0.53 | 0.15 ± 0.02 | 7.06 ± 0.42 b |

Means of triplicate runs ± standard deviation
[a]Fermentation Rate. Means followed by the same letter are similar (P < 0.05)

In organic acid profiles, final lactic acid concentrations remained below 0.09% (w/v) for all runs except 45% solids vacuum treatment, which had a concentration of 0.59% (w/v) (Table 2).

Acetic acid concentrations were negligible for all runs except 40 and 45% vacuum treatments, which had 0.03 and 0.15% (w/v), respectively. Acetic acid and lactic acid (as well as other organic acids) are known to inhibit yeast growth. Acetic acid, which inhibits membrane phosphate transport, is a minor by-product of the fermentation pathway but can be produced by acetic acid bacteria. Presence of lactic acid is indicative of lactobacillus contamination. It has been reported that the lactic acid minimum inhibitory concentration is 2.5% (w/v), but yeast can be stresses at 0.2 to 0.8% (w/v) (Narendranath, et al. (2001) supra). Similarly, it has been reported that the acetic acid minimum inhibitory concentration is 0.6% (w/v), however, yeast can be stressed at 0.05 to 0.1% (w/v) (Narendranath, et al. (2001) supra). The higher levels of lactic and acetic acid observed in 45% vacuum treatments suggested that, despite lower ethanol concentrations, other fermentation conditions may encourage contamination. Maiorella, et al. ((1983) *Adv. Biochem. Eng.* 20:43-92) found that vacuum stripping (as well as any other in situ technologies) concentrate nonvolatile metabolites, aggravating inhibition effects.

Glycerol is produced as yeast respond to hyperosmotic stress but also as a redox balance when surplus NADH is produced during anaerobic fermentation (Nordström (1966) supra; van Dijken & Scheffers (1986) supra). Glycerol levels typically reached near maximum value by 48 hours. For both conventional and vacuum treatments, 40% solids treatment had highest concentration, followed by 45 and 30% solids (Table 2). Higher glycerol levels produced in vacuum cycled treatments could result from a concentration effect (Maiorella, et al. (1983) supra). In dry grind, typical glyceryol levels range between 1.2 to 1.5% (v/v) (Russel (2003) Understanding *Saccharomyces* yeast fundamentals. Pages 103-110 in: The Alcohol Textbook: A Reference for the Beverage, Fuel and Industrial Alcohol Industries, 4th).

Ethanol yields at 30% solids, which were highest among solids treatments, were similar for conventional and vacuum treatments (Table 3). Ethanol yields, next highest, were similar for 40% solids conventional and vacuum treatments. For 45% solids, vacuum ethanol yields were 14% lower than conventional treatment yields. Vacuum stripping did not improve ethanol yields at any solids level.

Ethanol conversion efficiencies echoed trends with ethanol yield, decreasing with increasing solids content ($R2=0.95$) (Table 3). Distillate recovery increased with increasing solids content ($R2=0.95$) with 71% of total ethanol recovered in distillate for 45% solids treatments. Higher recoveries were due to an interaction between vacuum treatment and solids content; at higher solids a larger percent of beer volume is boiled off.

Logically, fermenting beers with higher solids contents resulted in beer and whole stillage with higher solids. For 45% solids treatments, conventional operation resulted in 32.2 and 39.5% (w/w) for beer and stillage solids, respectively (Table 4). For vacuum treatment, solids increased by 33% to 42.9% (w/w) for beer and by 24% to 49.0% (w/w) for stillage. For 40% solids, vacuum treatments increased by 28.8% to 29.5% (w/w) and stillage solids increased by 17.8% to 36.5% (w/w) compared to conventional treatment. Incomplete fermentations at 40 and 45% solids, with conversion near 64 and 43%, respectively, also contributed to these higher solids values. For 30% solids, conventional beer and stillage solids contents were 11.7 and 18.4% (w/w), respectively. With vacuum treatment, beer solids increased by 41.9% to 16.6% (w/w) and stillage solids increased by 13.6% to 20.9% (w/w).

TABLE 4

| Treatment | Beer Solids Content[a,b] % | Stillage Solids Content[a,c] % |
|---|---|---|
| 30% Conventional | 11.7 ± 0.5 a | 18.4 ± 1.2 g |
| 30% Vacuum | 16.6 ± 1.4 b | 20.9 ± 1.0 h |
| 40% Conventional | 22.9 ± 0.2 c | 30.9 ± 0.3 i |
| 40% Vacuum | 29.5 ± 0.8 d | 36.4 ± 1.1 j |
| 45% Conventional | 32.2 ± 0.6 e | 39.5 ± 0.9 k |
| 45% Vacuum | 42.9 ± 1.3 f | 49.0 ± 0.9 m |

Means of triplicate runs ± standard deviation.
[a]Means followed by the same letter are similar ($P < 0.05$).
[b]Fisher's LSD was 1.65% (w/w).
[c]Fisher's LSD was 1.67% (w/w).

Higher solids are desirable as dewatering after distillation can be reduced or avoided. By producing stillage with solids content >35%, as is the case with 40% vacuum and all 45% solids treatments, dewatering operations, which separate whole stillage to thin stillage and wet grains, would be unnecessary. Complications with lactic acid contamination from

TABLE 3

| Treatment | Ethanol Yield[a] L/kg[c] | Ethanol Yield[b] gal/bu[c] | Ethanol Conversion Efficiency[b] % | Ethanol Recovered in Distillate % |
|---|---|---|---|---|
| 30% Conventional | 0.360 ± 0.006 a | 2.41 ± 0.04 | 78.1 ± 1.3 | n/a |
| 30% Vacuum | 0.348 ± 0.002 a | 2.34 ± 0.02 | 75.6 ± 0.5 | 58.2 ± 7.2 |
| 40% Conventional | 0.287 ± 0.003 b | 1.93 ± 0.02 | 62.3 ± 0.6 | n/a |
| 40% Vacuum | 0.289 ± 0.002 b | 1.94 ± 0.01 | 62.8 ± 0.4 | 63.9 ± 1.3 |
| 45% Conventional | 0.208 ± 0.009 c | 1.40 ± 0.06 | 45.2 ± 2.0 | n/a |
| 45% Vacuum | 0.180 ± 0.013 d | 1.20 ± 0.09 | 39.0 ± 2.8 | 70.5 ± 4.1 |

Means of triplicate runs ± standard deviation.
[a]Mean total ethanol followed by the same letter are not significantly different ($P < 0.05$). Fishers LSD for mean ethanol yield was 0.015 (L/kg).
[b]Theoretical ethanol yield was 0.46 (L/kg) or 3.09 (gal/bu). Least significant difference results were same as for ethanol yield (L/kg).
[c]L/kg is liters ethanol per kg corn; gal/bu is gallons ethanol per bushel corn.

recycled thin stillage (Narendranath, et al. (1997) *Appl. Environ. Microb.* 63:4158-4163; Maiorella, et al. (1984) *Biotechnol. Bioeng.* 26:1155-1166) and fouling from stillage evaporative concentration (Singh, et al. (1999) *Cereal Chem.* 76:846-849; Wilkins, et al. (2006) *Cereal Chem.* 83:121-126) would be reduced. Furthermore, solids could be sold directly as wet grains. The superiority of wet distillers grain and DDGS as feeds over corn have been reporated, with higher energy value and feed efficiency than corn (Klopfenstein (1996) *Anim. Feed Sci. Technol.* 60:201-207).

As 45% solids produced a lower ethanol yield during vacuum treatment, the 40% solids treatment was selected for further analysis. During vacuum treatment, glucose concentration did not increase as observed during conventional treatment. If ethanol removal with vacuum stripping reduced product inhibition, then glucose uptake and ethanol production were expected to be higher during vacuum treatments, producing a higher ethanol yield. However, similar amounts of ethanol were produced between conventional and vacuum runs (Table 3), indicating that glucose was not converted to ethanol. To determine the cause of the lower than anticipated ethanol yields, several different analyses were conducted.

The Crabtree effect (Crabtree (1929) *Biochem. J.* 23:536-545; Deken (1966) *J. Gen. Microbiol.* 44:149-156) describes the phenomenon of aerobic alcohol fermentation and occurs between 0.3 to 10% (w/v) (Maiorella, et al. (1981) *Adv. Biochem. Eng.* 20:43-92). Glucose concentrations during vacuum cycling below 0.08 (w/v) along with repressurization with ambient air may have replenished oxygen levels in beer and induced a metabolic shift in yeast, albeit briefly, to aerobic growth. $CO_2$ was used to repressurize the bioreactor after vacuum cycling instead of ambient air; however, no improvement in ethanol yield was found.

Although no experiments on enzyme activity were conducted, enzyme performance could be inferred by analyzing glucose production and residual starch. Though the highest ethanol concentrations resulted from 40% solids fermentations, glucose production continued through fermentation completion (observed with the glucose increase at 40% solids). This observation indicated that ethanol inhibition of GSHE was not a significant factor.

During vacuum treatment, beer boiling or higher solids may adversely affect GSHE. A reduction in enzymatic performance would produce less glucose; accumulation would not be apparent. Residual starch analysis can be used to evaluate enzymatic performance indirectly by quantitating the starch remaining after fermentation. A higher percentage of residual starch from vacuum cycled beer would indicate a reduction in enzyme performance. Otherwise, similar or less starch would suggest similar or superior GSHE performance and that yeast cells may be at cause. Residual starch for 30% solids control was 31.3 and 29.2% w/w for conventional and vacuum treatments, respectively. Residual starch of conventional and vacuum treated fermentations at 40% solids was 43.7 and 45.5% (w/w) starch. Though similar, high residual starch indicated inadequate GSHE dose at higher solids. Higher residual starch at higher solids implied a solids effect. These results did not, however, account for the phenomenon surrounding the glucose increase.

If GSHE remained active similarly throughout conventional and vacuum treatments then higher cell densities during vacuum treatment could account for reduced ethanol yield. In situ ethanol removal provides for healthier cells with higher cell growth (Cysewski & Wilke (1977) supra; Casey & Ingledew (1986) supra; Thatipamala, et al. (1992) supra). Furthermore, removing ethanol and water concentrates non-volatile beer components, including yeast cells. Both conditions may contribute synergistically to higher yeast densities. Viable yeast density profiles were prepared for conventional and vacuum treatments at 40% solids. Conventional treatment yeast densities were in lag phase from 0 to 3 hours, then underwent logarithmic growth until 12 hours, reaching 229 mil cell/mL. During the stationary phase (12 to 30 hours) cell densities settled at 258 mil cell/mL before dropping to near zero by 72 hours. By 18 hours ethanol concentrations were at 11.6% (v/v), above stressing levels. The vacuum treatment profile was similar until 12 hours, after which the growth phase continued until 24 hours (383 mil cell/hr) before peaking at 36 hours (460 mil cell/hr). This density was 78% higher than the conventional treatment and industrial cell densities (Kelsall & Lyons (2003) *Grain dry milling and cooking procedures: extracting sugars in preparation for fermentation.* Pages 9-21 in: *The Alcohol Textbook: A Reference for the Beverage, Fuel and Industrial Alcohol Industries,* 4th. Jacques, et al., eds. Nottingham University Press: Nottingham, UK.). Considering the similar ethanol yields produced at 40% solids, residual glucose could have been consumed by cell overgrowth.

An effective method of controlling high yeast populations is by controlling substrate production, typically by lowering the enzyme dose. Yet results from residual starch analysis indicated that enzyme dose was inadequate. Therefore, to reduce yeast density, yeast inoculate was reduced by approximately half to 2.50 mL and, to increase starch digestion, GSHE dose was increased three-fold. Conventional and vacuum treatments at 40% solids were conducted in triplicate and compared to 40% solids at regular dose and inoculate.

Ethanol concentration at 72 hours for conventional treatments ranged from 19.1 to 19.3% (v/v). Concentrations were slightly higher than those from regular conventional treatments (18.9% v/v). For vacuum treatment final ethanol concentration ranged from 10.6 to 11.2% (v/v) with maximum ethanol concentration, occurring at 36 hours, below 14.0% (v/v). These levels were about 25% higher than regular vacuum treatments at 40% solids. Spurred by higher glucose production and reduced ethanol concentrations, yeast productivity to ethanol increased. Higher levels of ethanol were maintained. Initial glucose concentrations were 27% higher than 40% solids at regular treatment (LSD of 0.59% w/v). Glucose concentrations rose to 6.0% (w/v) before decreasing to 1% (w/v) at 12 hours, after which concentrations stabilized until 36 hours. Glucose concentrations then increased linearly to 3.2% (w/v) at 72 hours. The higher steady state glucose concentration was a result of higher GSHE dose. Glucose concentration for 3× GSHE dose vacuum treatment was similar up to 18 hours but remained <0.2% (w/v) through the remainder of the fermentation.

Fermentation rates were similar to regular treatment values at 40% solids (LSD of 0.65 g/L/hr). For 3× GSHE conventional treatment, fermentation completion was 79.6% of maximum at 24 hours and 99.5% of maximum at 48 hours. Lactic acid was below 0.05% (w/v) for 3× GSHE conventional and below 0.08% (w/v) for 3× GSHE dose vacuum treatment. Acetic acid remained below 0.04% (w/v) for conventional and negligible production for vacuum treatment. Glycerol concentration was 0.95 and 1.62% (v/v) for conventional and vacuum treatments, respectively. These values were comparable with regular treatment results.

Ethanol yield for 3× GSHE conventional treatment was similar to regular 40% solids vacuum treatment (Table 5). Ethanol yield for 3× GSHE vacuum treatment, however, increased by 21% to 0.355 L/kg (2.38 gal/bu), which was similar to results from control, 30% conventional treatment. Though this improvement resulted from an unoptimized, three fold increase in GSHE dose. GSHE was dosed at high levels to remove it as a limiting factor.

TABLE 5

| Treatment | Ethanol Yield L/kg | Ethanol Yield gal/bu | Ethanol Conversion Efficiency % | Ethanol Recovered in Distillate % |
|---|---|---|---|---|
| 40% Conventional | 0.294 ± 0.003 | 1.97 ± 0.02 | 63.8 ± 0.7 | n/a |
| 40% Vacuum | 0.355 ± 0.003 | 2.38 ± 0.02 | 77.1 ± 0.7 | 64.0 ± 0.9 |

Means of triplicate runs ± standard deviation.

Residual starch analysis of 3× treatments resulted in lower starch from vacuum treatment (25.6% w/w) than 3× GSHE conventional (43.7% w/w) or regular treatments (44.6% w/w). During the assay, starch is hydrolyzed to glucose; then GOPOD reacts with glucose quantitatively. The high final glucose concentrations observed during 3× GSHE conventional also reacted with GOPOD, increasing the determined residual starch. Regardless, more starch was hydrolyzed, reducing the total solids content of beer and whole stillage.

Beer solids content was 22.2 and 24.1% (w/w) for 3× GSHE conventional and vacuum treatments, respectively, while whole stillage solids content were 30.4 and 29.7% (w/w), respectively. Beer solids for 3× GSHE and regular conventional treatments were similar (LSD of 1.13% w/w). Conventional and vacuum stillage solids for 3× GSHE were similar to each other and to normal 40% conventional (LSD of 1.86% w/w).

Final yeast densities were near zero for 3× GSHE conventional treatment which was similar to regular 40% conventional treatments. For vacuum treatment final yeast density was 315 mil cell/mL, 21% lower than regular vacuum treatment. Higher ethanol yields were achieved despite lower yeast density, implying that enzyme dose was more critical than inoculate in producing higher ethanol yields.

Collectively, the results of this analysis indicated that using GSHE instead of conventional enzymes allows the use of higher slurry solids by eliminating limits imposed by liquefaction and glucose inhibition. After combining GSHE with vacuum stripping, ethanol yields comparable to conventional dry grind processes were produced by increasing enzyme dose significantly and reducing inoculate by half. The use of high solids could impact downstream processing by reducing capital and operation costs. Thin stillage is the effluent resulting from concentrating whole stillage (FIG. 1A from 10% solids to 35% solids). Approximately 30% of thin stillage is recycled, called "backset," for slurrying, saving capital and operating costs as effluent streams are reduced and overall water usage is reduced (Wall, et al. (1983) *J. Agric. Food. Chem.* 31:770-775; Chin & Ingledew (1993) *J. Agric. Food. Chem.* 41:1156-1163). However, buildup of nonmetabolized components like lactic and acetic acid in recycled thin stillage can inhibit enzymes and yeast (Maiorella, et al. (1983) supra; Maiorella, et al. (1984) supra). Furthermore, concentrating the remaining thin stillage to syrup causes heavy fouling in evaporators (Singh, et al. (1999) supra), which are expensive to maintain. Dry grind operation at higher solids could eliminate thin stillage production and reduce drying costs of DDGS.

The invention is described in greater detail by the following non-limiting examples.

EXAMPLE 1

Materials

Yellow dent corn (34N78, Pioneer Hi-Bred International, Johnston, Iowa) was obtained from the Agricultural and Biological Engineering Research Farm, University of Illinois at Urbana-Champaign.

For slurry preparation sulfuric acid (10N, Ricca Chemical Company, Arlington, Tex.), solid urea (U15-500, Fisher Scientific, Waltham, Mass.) and active dry yeast (*S. cerevisiae*) (Ethanol Red, Fermentis, Lesaffre Yeast Corporation, Milwaukee, Wis.) were used. The fermentation enzyme was a granular starch hydrolyzing enzyme (GSHE) (STARGEN® 001, Genencor, Palo Alto, Calif.) that contained α-amylase from *A. kawachi* and glucoamylase from *A. niger* and had activity of ≧456 GSHU/g (where GSHU=granular starch hydrolyzing units).

Figure 2:
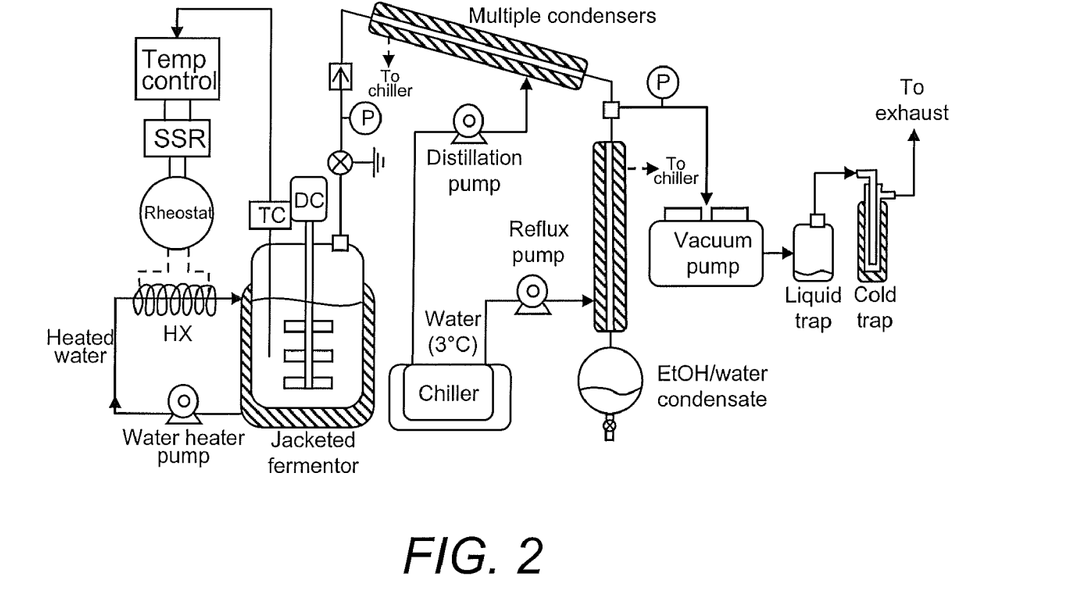

The vacuum stripping and fermentation apparatus was composed of a 3 L jacketed fermenter (Biostat MD, Sartorius BBI Systems, Edgewood, N.Y.) which was sealed with plastic and modified for thermocouple, vacuum and sample ports (FIG. 2). Slurry was agitated by paddle type blades. The agitator was driven at 30 rpm by a variable AC/DC motor drive (90 VDC, model KD P/N 3402-008, Hurst, Princeton, N.J.).

The fermenter was heated by circulating water through a shell heat exchanger surrounded by a resistive heating tape (310 W, B00051-060, Barnstead/Thermolyne, Dubuque, Iowa). Heating temperature (i.e., voltage) was limited by a rheostat (Powerstat model 3PN126, Superior Electric Co., Bristol, Conn.), which was triggered by a solid state relay (W6225DSX, Magnecraft, Northfield, Ill.) connected to a temperature controller (CNi1643, Omega, Stanford, Conn.).

The stripping system, connected to the fermenter through a check valve, included a 200 mm condenser (LG-5150-100 Liebig, Wilmad Lab Glass, Buena, N.J.) and a 300 mm condenser (LG-5150-104 Liebig) in series. The condensate continued through another 200 mm condenser (LG-5150-100 Liebig) and was collected in a 1000 mL round bottom flask (Z414522, Sigma Aldrich, St. Louis, Mo.) modified with a PTFE outlet valve. All glass joints were sealed with high vacuum grease (Dow Corning, Midland, Mich.). Cooling fluid was water chilled to 3° C. with a constant temperature refrigerated bath (MR-3220A-1, Blue M Electric Co, Blue Island, Ill.) and circulated with two peristaltic pumps (Masterflex 7520-00 with Easyload 75-18 pump head, Cole-Parmer, Chicago, Ill.). The chiller was controlled by a traceable time controller (7-day 5056-84, Fisher Scientific, Waltham, Mass.) to prepare chilled water ahead of vacuum cycling.

Vacuum was generated with a tunable PTFE dry vacuum pump (Dry Fast model 2044, Welch, Niles, Ill.). Vacuum pressure was monitored at two points, in the fermentation vessel with a vacuum gauge (45W1000, Ashcroft, Stratford, Conn.) and near the vacuum pump with pressure/vacuum gauge (7054-18R, Ashcroft, Stratford, Conn.). Vacuum exhaust was connected to a liquid trap (250 mL, C-5340-250, Wilmad Lab Glass, Buena, N.J.) and a cold trap (LG-11025-100, Wilmad Lab Glass, Buena, N.J.) chilled with 3° C. water to condense exhausting ethanol and water.

EXAMPLE 2

Conventional GSHE Fermentation

Corn was sieved over a 4.76 mm (12/64 in.) round hole screen and hand cleaned to remove heat damaged kernels and foreign material such as soybeans, corn silks, stones and dirt. Corn was fed by a vibrating feeder (F-TO, FMC Syntron, Tupelo, Miss.) to a hammer mill (SK100/S Spezialstahl, Retsch and GmbH and Co., Haan, Germany) and ground at 500 rpm through a 2.0 mm triangle hole sieve. Ground corn was analyzed for moisture content (Method 44-19; AACC (2002) Approved Methods of the American Association of Cereal Chemists, 10th ed. The Association: St. Paul, Minn.) and stored at 4° C. Slurry was prepared with 450 gram dry weight ground corn and water to specified solids and adjusted to pH 4.0 with sulfuric acid. Solid urea at 0.1 gram/100 gram dry corn was added as a nitrogen source. GSHE at 0.25 gram/100 gram dry corn was added based on manufacturer recommendations. Slurry was inoculated with *S. cerevisiae* at 0.24 gram/100 gram dry corn.

Slurry was added to the fermentor and agitated at 30 rpm. Higher solids contents required more torque from the agitator to achieve needed agitation. Enzymatic hydrolysis and fermentation gradually reduced beer viscosity. Therefore, agitation rates were reset to 30 rpm after each sample. The temperature controller was set to 32° C. and rheostat to 50%. The fermentation was run for 72 hours after inoculation. Samples (2 mL) were taken through the sample port with a 10 mL pipette at 4, 8, 12, 18, 24, 30, 36, 48 and 72 hours during fermentation.

EXAMPLE 3

Vacuum Stripping Method

Efforts have been made to keep ethanol concentrations below 1.3% (v/v) (Cysewski & Wilke (1977) supra). At this concentration, the boiling point of beer at torr is 35° C., the optimum growth temperature for the yeast strain disclosed therein. However, ethanol concentrations only need to be maintained below initial inhibitory levels (10 to 13% v/v; Casey & Inglewed (1986) *CRC Crit. Rev. Microbiol.* 13:219-280); at 50 torr beer will boil at 32° C. Accordingly, vacuum at 6.7 kPa (50 torr or 28 inHg) was selected for all treatments herein. Vacuum pressure varied by ±0.2 kPa (0.05 inHg) during the stripping operation. Vacuum was applied at 12, 18, 24, 36 and 48 hours after inoculation for 0.5 hours. Each application was called a vacuum cycle. Preliminary experiments indicated this cycling frequency was sufficient to maintain ethanol concentrations of all solids contents below inhibitory levels. For one treatment at each solids level, samples of beer were taken immediately after each vacuum cycle (at 12.5, 18.5, 24.5, 36.5 and 48.5 hours) to monitor the immediate effect of vacuum cycling on beer ethanol concentration.

The water chiller, set at 3° C., was turned on 2 hours before each vacuum cycle. The condenser system and reflux pumps were started, feeding chilled water through condensers. Vacuum was applied and the rheostat increased from 50 to 60% power (to counter evaporative cooling of the beer during stripping operation). Frothing, caused by $CO_2$ escape during initial vacuum application, was reduced by increasing agitation to 60 rpm and by gradually increasing vacuum to set point. At the completion of each vacuum cycle, vacuum was stopped and filtered air was introduced gradually to the system until pressure equilibrated to ambient. The mass of condensate was recorded and a subsample taken for HPLC analysis.

To collect residual ethanol, located throughout the stripping system, condensers were drained and the fermenter was sealed from vacuum, though chilled water continued flowing through the cold trap. Vacuum was applied at pump maximum (2.3 kPa or 29.3 inHg), for 0.5 hour. Components in the exhaust were condensed in liquid and cold traps. Condensates, containing residual ethanol, were combined and weighed; a subsample was prepared for HPLC analysis.

EXAMPLE 4

Use of Increased Amounts of GSHE During Fermentation

During 3× GSHE treatments fermentations were dosed with GSHE at three times manufacturer's recommendation and at reduced inoculate. GSHE was added at 0.75 gram/100 gram dry corn and slurry was inoculated at 0.11 gram/100 gram dry corn.

EXAMPLE 5

Use of $CO_2$ During Fermentation

For $CO_2$ treatments, carbon dioxide (Coleman grade 99.99% pure, S. J. Smith, Urbana, Ill.), instead of air, was introduced into the fermenter after each vacuum cycle. Carbon dioxide was used to maintain an anaerobic environment.

EXAMPLE 6

Assay Procedures

Metabolite Profiles. Fermentation, distillate and whole stillage samples were analyzed via HPLC (Column: Aminex HPX-87H organic acid, BIORAD, Hercules, Calif.; System: Breeze, Waters Corp, Milford, Mass.) for ethanol (% v/v), glucose (% w/v), glycerol (% v/v), lactic acid (% v/v) and acetic acid (% v/v). Ethanol and glucose were used to analyze fermentation progress. Organic acids such as acetic acid ($\geq 0.05\%$ w/v) and lactic acid ($\geq 0.2\%$ w/v) are known to stress and inhibit yeast productivity (Narendranath, et al. (2001) *J. Ind. Microbiol. Biotechnol.* 26:171-177) and were monitored throughout fermentation. Glycerol production, indicative of hyperosmotic stress or excess NADH (Nordström (1966) *Acta Chem. Scand.* 20:1016-1025; van Dijken & Scheffers (1986) *FEMS Microbiol. Rev.* 32:199-224), was used to monitor yeast response to the higher solids.

Beer samples were centrifuged for three minutes at 11,000×g (Model 5425, Eppendorf, Westbury, N.Y.). Samples from higher solids beers, which were more viscous, were centrifuged for 5 to 10 minutes. The supernatants were filtered through a 0.2 µm filter into a 0.2 mL vial insert. Distillate samples, usually with ethanol concentrations between 30 and 50% (v/v), were diluted with distilled water to 4× before analysis.

Beer and Whole Stillage Solids Content. Fermentation beer was weighed and a 15 gram sample taken for moisture content analysis in triplicate (Method 44-19; AACC (2002) supra). Beer solids were calculated as the compliment of the moisture content. Whole stillage is composed of the solids remaining after ethanol and water removal during distillation. To emulate this process at the bench scale, beer was heated to produce a single stage distillation. The remaining beer was added to a 3 L fermentation vessel (1965-83000, Bellco Glass, Vineland, N.J.) and agitated at 50 rpm with an overhead drive (7774-10115, Bellco Glass, Vineland, N.J.) for 3 hours in a waterbath (Precision, Jouan Inc, Winchester, Va.) at 90° C. Stillage solids content was analyzed in triplicate, similarly to beer.

Residual Starch Analysis. Total residual starch of 40% solids whole stillage samples was measured using an acid hydrolysis method. Hydrocholoric acid (0.4 M) was prepared by diluting 66.2 mL concentrated HCl (A144C-212, Fisher Scientific, Waltham, Mass.) into 1.5 L distilled water and brought to volume in a 2 L volumetric flask. Sodium carbonate solution (2 M) was prepared by dissolving 24.8 gram $Na_2CO_3 \cdot H2O$ (Acros Organics, Geel, Belgium) in 80 mL distilled water and brought to volume in a 100 mL volumetric flask. The volume required to buffer 10 mL of 0.4 M HCl with 2 M $Na_2CO_3$ was determined for each newly prepared batch of HCl or sodium carbonate solution (approximately 1.1 mL). Glucose oxidase and peroxidase (GOPOD) reagent buffer was prepared from the Total Starch Kit (Megazyme, Wicklow, Ireland).

Stillage samples were dried overnight at 49° C., ground in a coffee grinder (Black and Decker, Towson, Md.) and analyzed for moisture content (Method 44-19; AACC (2002) supra). Stillage samples (1.000 gram) were weighed in duplicate into 125 mL autoclave-safe bottles. Controls of glucose (D(+)-glucose anhydrous, Acros Organics, Geel, Belgium) and starch (HYLON® V Corn Starch, National Starch Food Innovation, Bridgewater, N.J.) were prepared with stillage samples, in triplicate. To each bottle, 50 mL of 0.4 M HCl was added. Bottles were capped loosely and autoclaved for 80 minutes at 260° C. After cooling to room temperature in an ice bath, 10 mL of each sample was transferred to a 50 mL centrifuge tube, buffered to pH 7 with the previously determined volume of 2 M $Na_2CO_3$ solution, and vortexed. Samples were centrifuged for 10 minutes at 800×g. Stillage samples were diluted to 8× or 16× while glucose and starch samples were diluted to 40×; 0.1 mL was transferred to a 15 mL centrifuge tube. A blank was prepared with 0.1 mL distilled water. Glucose standards of 0.25, 0.50, 0.75 and 1.00 mg/mL were prepared from a 1.00 mg/mL standard solution; 0.1 mL was transferred to 15 mL centrifuge tubes. To each centrifuge tube, 3 mL GOPOD reagent was added; tubes were vortexed and incubated in a 50° C. water bath (Gyromax 939XL, Amerex Instruments, Lafayette, Calif.) for 20 minutes. Solutions were read at 510 nm on a spectrophotometer (Helios γ, Thermo Scientific, Needham Heights, Mass.).

An absorbance calibration curve was prepared from the glucose standards. Glucose recovery was determined from the glucose control and used to estimate sample loss throughout the assay. Percent starch was determined by multiplying the observed concentration by the dilution and recovery factors and dividing by 1.111, the molecular weight ratio of glucose to starch. The starch control was used to determine repeatability.

Enumeration of Viable Yeast Cells. Stock solution was prepared by mixing 34 gram $KH_2PO_4$ with 500 mL distilled water. Solution pH was adjusted to 7.2 with 1N NaOH (Fisher Scientific, Waltham, Mass.) and brought to volume in a 1 L volumetric flask. Phosphate buffer was prepared by adding 1.25 mL stock solution to 1 L distilled water followed by autoclaving for 20 minutes at 121° C. Fermentation samples (1 mL) were diluted between 103× and 106× in buffer. Duplicate PETRIFILMS (Yeast and Mold, 3M, St. Paul, Minn.) were inoculated with 1 mL of the diluted sample and incubated at room temperature for 5 days. Densities were reported in millions of cells per milliliter (mil cell/mL).

EXAMPLE 7

Data Analysis

Total Ethanol Yield. Eqn (1) and (2) were derived to determine the mass of ethanol in beer, distillate and residual condensate based on total liquid weight and ethanol concentration. Beer liquid weight was determined by multiplying the moisture content of beer by the total weight of beer. Distillate and exhaust loss weight were taken as is.

$$W_{Total\ Liquids} = W_{EtOH} + W_{H_2O} \quad (1)$$

$$[EtOH]_{Beer} = \frac{V_{EtOH}}{V_{EtOH} + V_{H_2O}} \quad (2)$$

where W is weight of ethanol or water, [EtOH] is volumetric ethanol concentration, and V is volume of ethanol or water.

Liquid components with highest concentrations were water, ethanol and glycerol with typical concentrations near 86, 13 and 1% (v/v), respectively. As ethanol and water constituted 98% of the sample liquid weight, glycerol had a negligible effect on ethanol and water volumes; the solution for an ethanol-water-glycerol system resulted in <1% difference in ethanol and water weights compared to the ethanol-water system. Accuracy was analyzed by HPLC analysis of prepared ethanol solutions, indicating a <2% error in ethanol weight and <0.2% error in water weight. The solution to the system is $$W_{H_2O} = \frac{W_{Total\ Liquids}}{\left(\frac{[EtOH]_{Beer}}{1 - [EtOH]_{Beer}}\right)\left(\frac{\rho_{EtOH}}{\rho_{H2O}}\right) + 1} \quad (3)$$

$$W_{EtOH} = W_{H2O}\left(\frac{[EtOH]_{Beer}}{1 - [EtOH]_{Beer}}\right)\left(\frac{\rho_{EtOH}}{\rho_{H2O}}\right) \quad (4)$$

where ρ is density of ethanol (0.7767 g/mL) or water (0.9941 g/mL) at 35° C., the HPLC operating temperature. Adding beer, distillate and residual ethanol gave total ethanol yield.

Total Ethanol Conversion. Starch and moisture content of whole corn was analyzed in quadruplicate using near infrared reflectance transmittance (OmegAnalyzer, DICKEY-John, Auburn, Ill.). Mean moisture was 12.8% (wb) and mean starch was 72.3% (db). Starch was multiplied by 1.111 and 0.511 to determine theoretical ethanol yield. Total ethanol conversion was calculated by dividing the actual ethanol yield by the theoretical ethanol yield, in this case 0.461 L/kg or 3.09 gal/bu.

Fermentation Rate and Completion. Fermentation rate was calculated as the change in ethanol concentration (g/L) during the first 12 hours of fermentation. Fermentation completion (g/L/hr) was calculated as the ethanol concentration divided by the final ethanol concentration.

EXAMPLE 8

Experimental Design

The hypothesis being tested was whether vacuum application improved ethanol productivity during high solids fermentation. Fermentations were conducted at 30 (control), 40 and 45% solids contents. Control was the average solids content in the dry grind industry, while 40 and 45% solids were used to test system response and ethanol yields at higher solids fermentations. The 40 and 45% solids treatments used 38 and 51% less water, respectively, than control. Application of vacuum stripping to a fermentation was a factor. Vacuum stripping entailed applying vacuum at 6.7 kPa (28 inHg) for 0.5 hour at 12, 18, 24, 36 and 48 hours after the start of the fermentation.

The factors were combined (3 solids levels with and without vacuum stripping), giving 6 treatments. A completely randomized design was carried out in triplicate for a total of 18 observations. Variables such as temperature, yeast dosage, vacuum pressure and cycling frequency were held constant as previously described. Two factor analysis of variance (ANOVA) with $\alpha$=0.05 was used to test whether ethanol yields from vacuum cycled treatments were greater than ambient pressure fermentations at each solids content level. Fisher's least significant differences (LSD) was used to identify the sources of rejection within the group.

What is claimed is:

1. A method for facilitating the fermentation of a high solids composition comprising subjecting a high solids composition to granular starch hydrolyzing enzyme under reduced pressure thereby facilitating the fermentation of the high solids composition.

2. The method of claim 1, wherein the high solids composition is at least 40% solids.

3. The method of claim 1, wherein said method is carried out in the absence of liquefaction and jet cooking steps.

4. The method of claim 1, wherein the granular starch hydrolyzing enzyme (GSHE) is employed at a rate of at least 0.75% weight GSHE per weight dry plant material.

5. The method of claim 1, wherein the reduced pressure is applied at intervals during fermentation.

* * * * *